(12) United States Patent
Faught et al.

(10) Patent No.: US 10,946,143 B2
(45) Date of Patent: Mar. 16, 2021

(54) DETECTION AND COMMUNICATION OF PLUNGER POSITION USING INDUCTION

(71) Applicant: West Pharmaceutical Services, Inc., Exton, PA (US)

(72) Inventors: Stacy Faught, Scottsdale, AZ (US); Jorge Santos, Scottsdale, AZ (US); Doug Owen Crow, Brownsboro, TX (US)

(73) Assignee: WEST PHARMACEUTICAL SERVICES, INC., Exton, PA (US)

( * ) Notice: Subject to any disclaimer, the term of this patent is extended or adjusted under 35 U.S.C. 154(b) by 0 days.

(21) Appl. No.: 16/615,948

(22) PCT Filed: May 25, 2018

(86) PCT No.: PCT/US2018/034605
§ 371 (c)(1),
(2) Date: Nov. 22, 2019

(87) PCT Pub. No.: WO2018/218128
PCT Pub. Date: Nov. 29, 2018

(65) Prior Publication Data
US 2020/0405964 A1  Dec. 31, 2020

Related U.S. Application Data

(60) Provisional application No. 62/511,086, filed on May 25, 2017.

(51) Int. Cl.
*A61M 5/315* (2006.01)
*A61M 5/31* (2006.01)

(52) U.S. Cl.
CPC ...... *A61M 5/31511* (2013.01); *A61M 5/3129* (2013.01); *A61M 5/31525* (2013.01);
(Continued)

(58) Field of Classification Search
CPC ............ A61M 5/31511; A61M 5/3129; A61M 5/31525; A61M 2205/18;
(Continued)

(56) References Cited

U.S. PATENT DOCUMENTS

| 2015/0174342 A1 | 6/2015 | Mitrosky et al. |
| 2016/0074587 A1* | 3/2016 | Searle .................. G01R 33/072 604/189 |

(Continued)

FOREIGN PATENT DOCUMENTS

| CN | 101380493 A | 3/2009 |
| CN | 101862488 A | 10/2010 |

(Continued)

OTHER PUBLICATIONS

Office Action dated Apr. 26, 2020 in Chinese Application No. 201880034624.1.
Int'l Search Report and Written Opinion dated Aug. 8, 2018 in Int'l Application No. PCT/US2018/034605.

*Primary Examiner* — Lauren P Farrar
(74) *Attorney, Agent, or Firm* — Panitch Schwarze Belisario & Nadel LLP

(57) ABSTRACT

A syringe system, including a plunger, a microcontroller, a battery, and a coil. The syringe barrel having a proximal end, a distal end, and a cylindrical sidewall defining a longitudinal axis, the cylindrical sidewall extending longitudinally between the proximal and distal ends, the sidewall having an exterior surface and defining an internal volume, the plunger being positioned between the proximal and distal ends of the syringe barrel and being movable within the internal volume with respect to the syringe barrel in the longitudinal direction. The syringe barrel further includes a label disposed on the sidewall and having at least two conductive strips extending in a non-parallel direction with respect to the longitudinal axis and having unique lengths. The microcon- (Continued)

troller is configured to determine a position of the plunger with respect to the syringe barrel by measuring a current induced in the coil by the at least two conductive strips.

14 Claims, 4 Drawing Sheets

(52) U.S. Cl.
CPC . *A61M 2205/18* (2013.01); *A61M 2205/3317* (2013.01); *A61M 2205/3368* (2013.01); *A61M 2205/3561* (2013.01); *A61M 2205/50* (2013.01); *A61M 2205/8206* (2013.01)

(58) Field of Classification Search
CPC .. A61M 2205/3317; A61M 2205/3368; A61M 2205/3561; A61M 2205/50; A61M 2205/8206
See application file for complete search history.

(56) References Cited

U.S. PATENT DOCUMENTS

2016/0213834 A1 7/2016 Brady et al.
2017/0312445 A1* 11/2017 Mirov .................. A61M 5/315

FOREIGN PATENT DOCUMENTS

| CN | 101862489 A | 10/2010 |
| CN | 203169740 U | 9/2013 |
| CN | 103656796 A | 3/2014 |
| CN | 104519931 A | 4/2015 |
| CN | 104721915 A | 6/2015 |
| CN | 104918649 A | 9/2015 |
| CN | 104936641 A | 9/2015 |
| WO | 2014111343 A1 | 7/2014 |
| WO | 2016140853 A1 | 9/2016 |

* cited by examiner

DETECTION AND COMMUNICATION OF PLUNGER POSITION USING INDUCTION

CROSS-REFERENCE TO RELATED APPLICATIONS

This application is a section 371 of International Application No. PCT/US2018/034605, filed May 25, 2018, which was published on Nov. 29, 2018 under International Publication No. WO 2018/218128 A1, and which claims priority to U.S. Provisional Patent Application No. 62/511,086, filed May 25, 2017, the entire contents of each of which are incorporated herein by reference.

BACKGROUND

It has been observed in a fast-growing healthcare system that patient adherence to drug programs impacts the cost to stakeholders. The effort to confirm adherence in low cost devices, such as prefilled syringes, has lagged more than other complex delivery systems in terms of connectivity. This is primarily due to the cost of the communication tools, many of which may cost more than the product itself.

One problem sometimes exhibited by prefilled syringes is the unwanted movement of their plungers during transit. Internal/external differential pressure changes due to, for example, changes in temperature or atmospheric pressure, may cause the plunger to move during air shipment and/or travel through different elevations. The movement of the plunger can affect product sterility. Another problem is the invasiveness of other potential solutions. Low cost injection devices, like prefilled syringes, have extremely strict manufacturing standards regarding modifications to the size, shape, and materials of the barrel and syringe plunger.

BRIEF SUMMARY

In an exemplary embodiment of the present disclosure, a syringe system is disclosed. The syringe system having a plunger including a microcontroller, a battery, and a coil connected to the microcontroller and the battery by two or more electrical leads. A syringe barrel has a proximal end, a distal end, and a cylindrical sidewall defining a longitudinal axis, the cylindrical sidewall extending longitudinally between the proximal and distal ends. The sidewall has an exterior surface and defines an internal volume. The plunger is positioned between the proximal and distal ends of the syringe barrel and is movable within the internal volume with respect to the syringe barrel in the longitudinal direction. The syringe barrel further includes a label disposed on the sidewall and formed by at least two conductive strips extending in a non-parallel direction with respect to the longitudinal axis and having unique lengths. The microcontroller is configured to determine a position of the plunger with respect to the syringe barrel by measuring a current induced in the coil by the at least two conductive strips.

In some embodiments of the system, the plunger includes a head section, at least a portion of which extends outside of the syringe barrel, and the battery and the microcontroller are disposed in the head section.

In some embodiments, the system further includes a temperature sensor configured to output a signal representative of a temperature of the syringe system to the microcontroller.

In some embodiments, the system further includes a wireless communication interface. The microcontroller is configured to transmit the temperature data received from the temperature sensor to a smart device via the wireless communication interface.

In some embodiments, the system further includes a wireless communication interface. The microcontroller is configured to transmit plunger position data to an external device via the wireless communication interface.

In some embodiments, the external device is configured to provide an alert to a user if the plunger position is determined by the microcontroller to have moved in excess of a predetermined distance.

In some embodiments, the microcontroller is configured to periodically cause the battery to supply the current to the coil at predetermined intervals.

In some embodiments, the at least two conductive strips are transparent.

In some embodiments, the at least two conductive strips are arranged on the sidewall of the barrel so as to be spaced apart from one another in the longitudinal direction, and are arranged in order according to circumferential length.

In another exemplary embodiment of the present disclosure, a method of using a syringe system is disclosed. The system including a plunger having a microcontroller, a battery, and a coil connected to the microcontroller and battery by two or more electrical leads. The syringe system further includes a syringe barrel defining a longitudinal axis and receiving the plunger, and a label disposed on a sidewall of the syringe barrel and having at least two conductive strips extending in a non-parallel direction with respect to the longitudinal axis and having unique lengths. The method includes generating, by the microcontroller, an eddy current in the coil by causing the battery to supply a current to the coil via the two or more electrical leads. An amplitude of the generated eddy current depends on a relative position of the coil with respect to each of the conductive strips of the label along a longitudinal direction of the syringe barrel. The method further includes measuring, by the microcontroller, the generated eddy current in the coil via the two or more electrical leads, and determining, by the microcontroller based on the measured eddy current, a position of the plunger with respect to the syringe barrel.

In some embodiments, the method can further include transmitting, by the microcontroller via a wireless communication interface, data regarding the determined plunger position to an external device.

In some embodiments, the method can further include generating, by the external device, one or more alerts based on data regarding the plunger position.

In some embodiments, the method can further include generating, by a temperature sensor, temperature data based on a measured temperature of the syringe system; and transmitting, by the microcontroller via a wireless communication interface, the temperature data to an external device.

In some embodiments, the method can further include generating, by the external device, one or more alerts based on the temperature data.

BRIEF DESCRIPTION OF THE DRAWINGS

Various aspects of the disclosure will now be described in connection with the attached drawings. For the purpose of illustration, there are shown in the drawings embodiments which are presently preferred. It should be understood, however, that the invention is not limited to the precise arrangements and instrumentalities shown.

DETAILED DESCRIPTION

Figure 1:
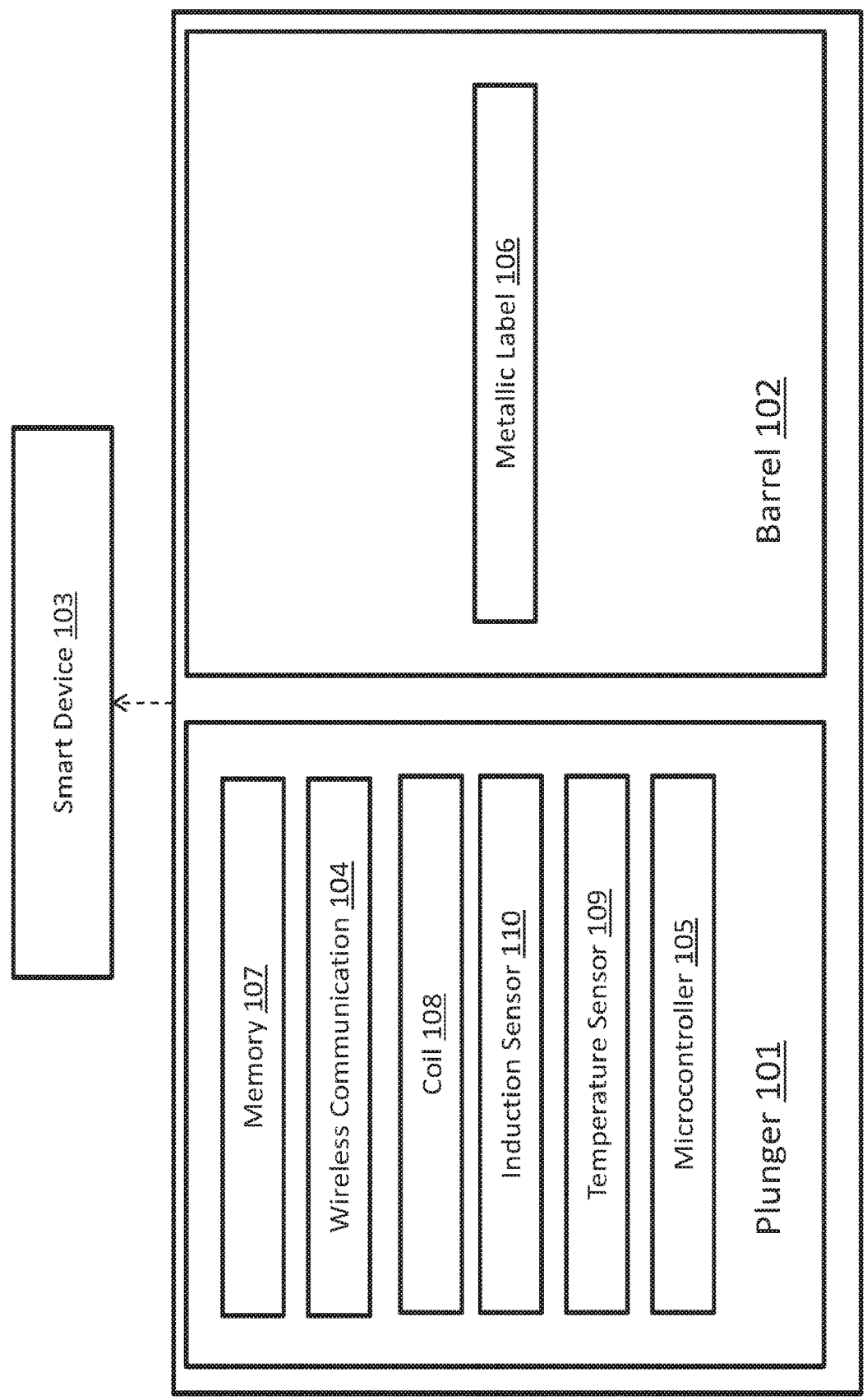
FIG. 1 is a block diagram depicting features of the syringe system, in accordance with a preferred embodiment of the present invention.

Certain terminology is used in the following description for convenience only and is not limiting. The words "right," "left," "lower," and "upper" designate directions in the drawings to which reference is made. The words "inwardly" and "outwardly" refer to directions toward and away from, respectively, the geometric center of the apparatus and designated parts thereof. The terminology includes the above-listed words, derivatives thereof, and words of similar import. Additionally, the words "a" and "an," as used in the claims and in the corresponding portions of the specification, mean "at least one."

The present disclosure may provide an affordable, scalable method of electrical communication to a drug delivery device, such as a single use syringe system 100, through the use of electrical induction. FIG. 1 is a block diagram depicting features of the syringe system, in accordance with aspects described herein. The syringe system 100 preferably includes at least a plunger 101 and a syringe barrel 102. The plunger 101 may be manually or automatically operated to apply pressure within the syringe barrel 102 such that a medicament (not shown) within the syringe barrel 102 can be dispensed through an opening, such as a needle 301. The syringe system 100 preferably allows for communication of status information (e.g., completion of an injection, movement of the plunger 101, temperature information, and the like) to an external device 103, such as a smart device, which may include a smart phone, tablet, personal computer, or other digital medical system or the like, through Bluetooth Low Energy or other wireless protocols via a wireless communication interface 104. Information regarding the position of the plunger 101 is preferably generated using electrical induction generated in a conductive coil 108 wrapped around or within the plunger 101, in conjunction with a microcontroller 105, which, in certain aspects, may be a Cypress PSoC 6 32-bit internet-of-things microcontroller or the like, and which is preferably embedded within the plunger 101.

The syringe barrel 102 preferably includes a label 106 formed thereon or affixed thereto, preferably on an outer surface of the syringe barrel 102. The label 106 may be placed on the outer circumference or an inner circumference of the syringe barrel 106, although the label 106 may also be embedded within a material of the syringe barrel 102. The label 106 preferably includes varying amounts of a conductive substrate running along a length of the label 106 in a longitudinal direction of the syringe barrel 102. In a preferred embodiment, the label 106 preferably includes a plurality of conductive strips 303 (FIG. 3), each of which extends in a circumferential direction, which may include a non-parallel direction with respect to a longitudinal axis of the syringe barrel 102, on the sidewall 304 of the syringe barrel 102. At least two of the conductive strips 303 have unique lengths, and preferably, each of the conductive strips 303 has a unique length. In another embodiment not shown, the conductive strips 303 may be oriented at an angle. Each of the conductive strips may be oriented at the same angle or at different angles. In these embodiments, each of the conductive strips 303 may have a unique effective length, which is the transverse length of the conductive strip 303 (i.e., the cosine of the pitch angle with respect to the longitudinal axis multiplied by the overall length of the conductive strip 303). Thus, conductive strips having the same overall length could be arranged at different angles to provide an array of strips each having a unique effective length. In the embodiment shown in FIG. 3, the overall length for each strip is the same as the unique effective length thereof. Consequently, as used herein, the term "unique length" will also refer to the unique effective length. The conductive strips 303 are preferably spaced apart from one another in the longitudinal direction on the syringe barrel 102 and may be arranged in order according to circumferential length (e.g., the longest strip may be adjacent one end of the syringe barrel 102 while the shortest strip can be adjacent to the other end). The conductive strips 303 may be composed of materials including, but not limited to, carbon, silver, copper ink, or the like. In certain aspects, one or more of the conductive strips 303 may be printed using a transparent conductive material. In other embodiments, each of the conductive strips may be comprised of a wire.

In other aspects, the label 106 may also be placed on other elements nearby, such as in the case of a syringe accessory, auto injector, or wearable drug delivery device (not shown), if it is in close enough proximity to the conductive coil 108 located on the plunger 101 to induce eddy currents therein. As described in further detail below, depending on a location of the plunger 101 with respect to the syringe barrel 102, and more particularly, a location of the coil 108 with respect to the label 106, the microcontroller 105 preferably measures a different eddy current produced by electrical induction generated in the coil 108 of the plunger 101 in part by a combined transverse length of the conductive strips 303 present at the particular location of the label 106.

The detected position is preferably written to a memory 107 in the plunger 101 to record, for example, any unintentional movement of the plunger 101 during transport. The memory 107 is preferably powerless, but can also be powered by a battery 202 (FIG. 2) or other power source. The microcontroller 105 may also use an embedded temperature sensor 109 to detect the temperature of the plunger 101, and may also write this temperature data to the memory 107 at a predetermined time interval, which may allow a temperature history of the syringe system 100 to be tracked to ensure proper cold chain integrity. In certain aspects, the syringe system 100 may alert the user, for example via the external device 103, of deviations from proper storage temperature conditions. This feature may also be used to notify a user that the medicament is at the proper temperature for injection after it has been removed from cold chain storage. Additionally, the detection of the plunger 101 positions may allow a user to see when and how much of a dose was administered to help ensure adherence and proper drug dosing.

The use of a microcontroller 105 and induction sensor 110 in accordance with aspects of the present invention may help reduce the cost of a plunger tracking system compared to some other potential solutions by eliminating the number of components needed, and may also allow for the tracking of the movement of the plunger 101 during transport. For example, the low energy microcontroller 105 may determine if there has been a change in position of the plunger 101 by sampling at predetermined intervals. In certain embodiments, the interval may be one second or shorter. If a change in the position of the plunger 101 is detected, the microcontroller 105 may start to record data and transmit to the connected smart device 103 via the wireless communication interface 104. The smart device 103 may alert the user that a change in the position of the plunger 101 has been detected.

The syringe system 100 may also be able to track and record the temperature thereof, and the length of time since the syringe barrel 102 was filled, by using an internal clock (not shown) of the microcontroller 105, as well as the on-board temperature sensor 109, which may be used to measure the temperature at a pre-set interval. The microcontroller 105 may write the temperature data to the memory 107 during an 'active' duty cycle of the microcontroller 105.

In certain aspects, the electronics used in this disclosure may be low-cost and small enough in scale to use on prefilled syringes and other injection devices. It may also be scaled to fit larger devices. The microcontroller 105 may have considerable power savings over previously created systems through the use of ultra-low boot cycles and a considerable 'inactive' duty cycle, which may minimize power drain and idle time.

Figure 2:
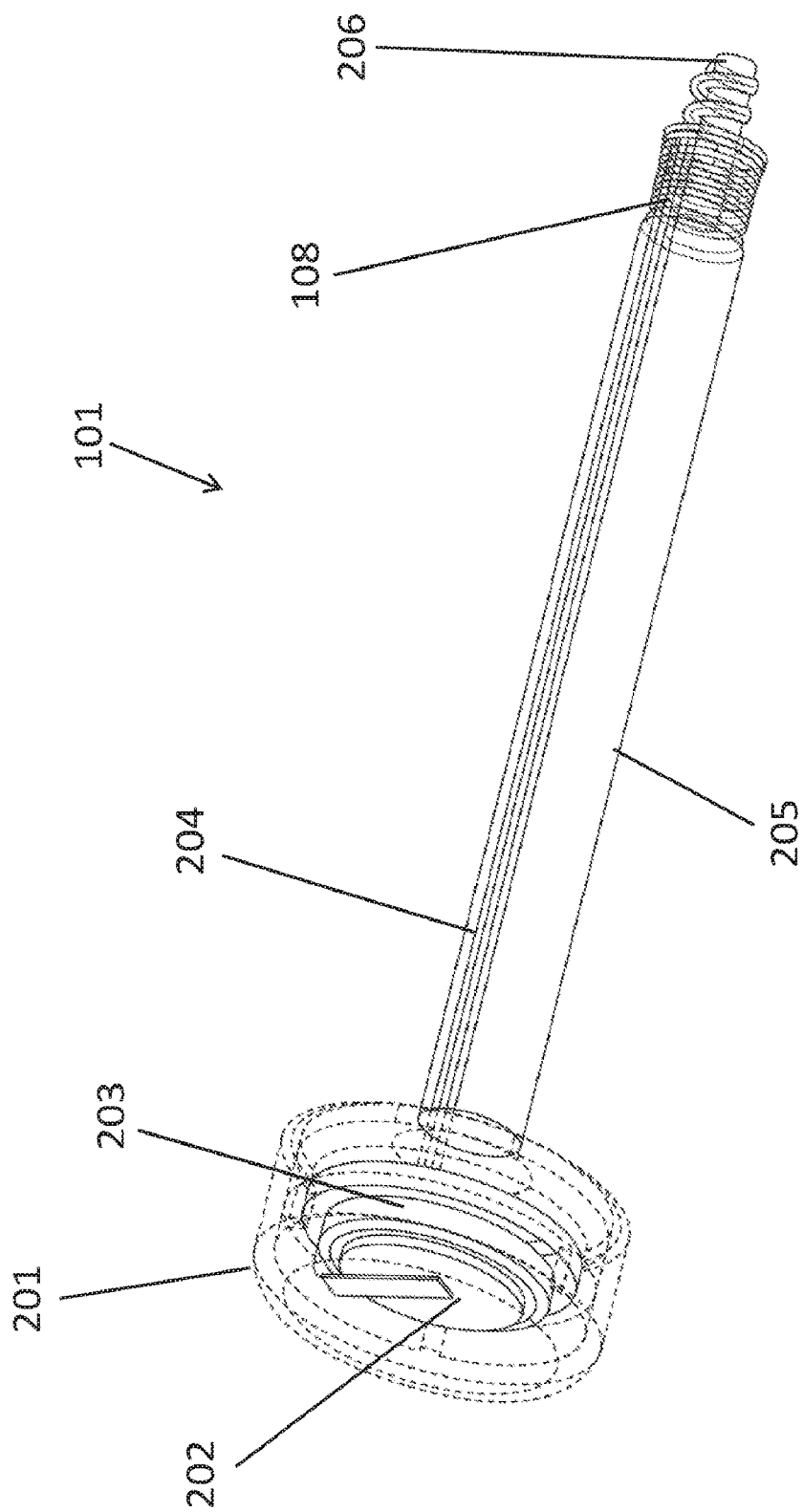
FIG. 2 is a perspective view of a plunger for a syringe system, in accordance with a preferred embodiment of the present invention.

FIG. 2 is a perspective view of the plunger 101 for use in an embodiment of the syringe system 100. The plunger 101 may use the battery 202 (such as a CR1220) to provide power to the coil 108, the microcontroller 105, and/or other components thereof. In certain aspects, the battery 202 may be rechargeable. The plunger 101 may house the battery 202 within a head section 201 at one end of the plunger 101. The head section 201 may also contain the microcontroller 105 (not shown in FIG. 2), which may be mounted to a printed circuit board 203. A set of two or more electrical leads 204 preferably runs from the microcontroller 105 in the head section 201 through a shaft 205 of the plunger 101, to where the leads 204 connect and transmit electrical signals to and from the coil 108 at a distal end of the plunger 101 opposite to the head section 201. The battery 203 and microcontroller 105 may be located on top of the syringe plunger 101 with the electrical leads 204 running from the microcontroller 105 to the piston 206, which may contain a locking mechanism (not shown) for a medicament delivery system.

In a preferred embodiment, the battery 203 periodically supplies current to the coil 108 through the electrical leads 204. By supplying current to the coil 108, an electrical induction field is generated at the coil 108 that can interact with the conductive strips 303 (FIG. 3) present on the label 106 disposed on the syringe barrel 102, which can be used to induce one or more eddy currents in the coil 108. The amplitude of the eddy current induced in the coil 108 depends at least in part on a relative position of the coil 108 with respect to each of the conductive strips 303 in the label 106 along the longitudinal direction of the syringe barrel 102 at the time the battery 203 supplies the current. The eddy current is influenced by one or more of the conductive strips 303 that are closest to the coil 108 when the current is applied, and the unique lengths of the conductive strips 303 distinguish the magnitude of the eddy current depending on the relative location of the coil 108. The microcontroller 105 measures the induced eddy current via the electrical leads 204, and interprets and converts the measurement into data representing a position of the plunger. In some embodiments, the microcontroller 105 is configured to periodically cause the battery 203 to supply current to the coil 108 at predetermined intervals. For example, the battery 203 may supply current every second, every five seconds, every minute, or any other interval. The microcontroller 105 may, in such embodiments, also determine the plunger position at these same supplying intervals.

Figure 3:
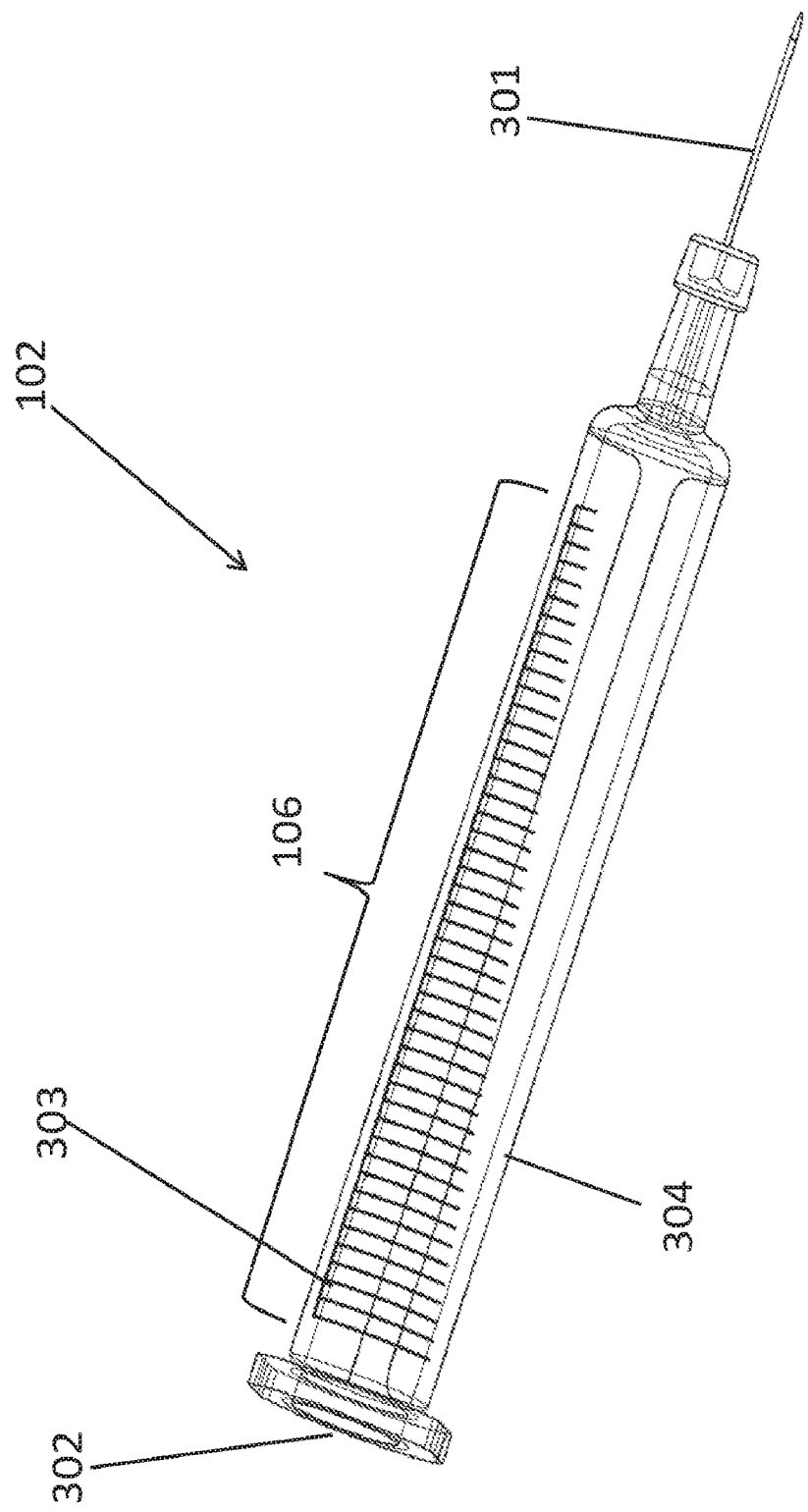
FIG. 3 is a perspective view of a syringe barrel for a syringe system, in accordance with a preferred embodiment of the present invention.

FIG. 3 illustrates a syringe barrel 102 for a syringe system 100, in accordance with aspects disclosed herein. In certain embodiments, the syringe barrel 102 may have the label 106 with one or more conductive strips 303 of varying size arrayed in a smallest-to-largest or largest-to-smallest configuration. In certain aspects, the smaller conductive strips 303 provide a smaller inductive force on the coil, while the larger conductive strips 303 may provide a larger inductive force on the coil. The configuration of metal printing of the label 106 may be in several forms, with the configuration shown in FIG. 2 shown as only one exemplary aspect of the configuration.

The syringe barrel 102 has a proximal end and a distal end and a cylindrical sidewall 304 extending longitudinally therebetween. The sidewall 304 has an exterior surface and defines an internal volume within which medicament may be stored. A barrel opening 302 is preferably located at the proximal end of the syringe barrel 102 and may be configured to accept medicament containers, such as drug ampules or vials. The plunger 101 may also preferably be inserted into the barrel opening 302 during manufacture and for transport, with the plunger 101 being movable within the internal volume of the syringe barrel 102 with respect thereto in the longitudinal direction for dispensing medicament. The medicament may be dispensed through a needle 301 or other delivery mechanism at the distal end of the syringe barrel 102.

Figure 4:
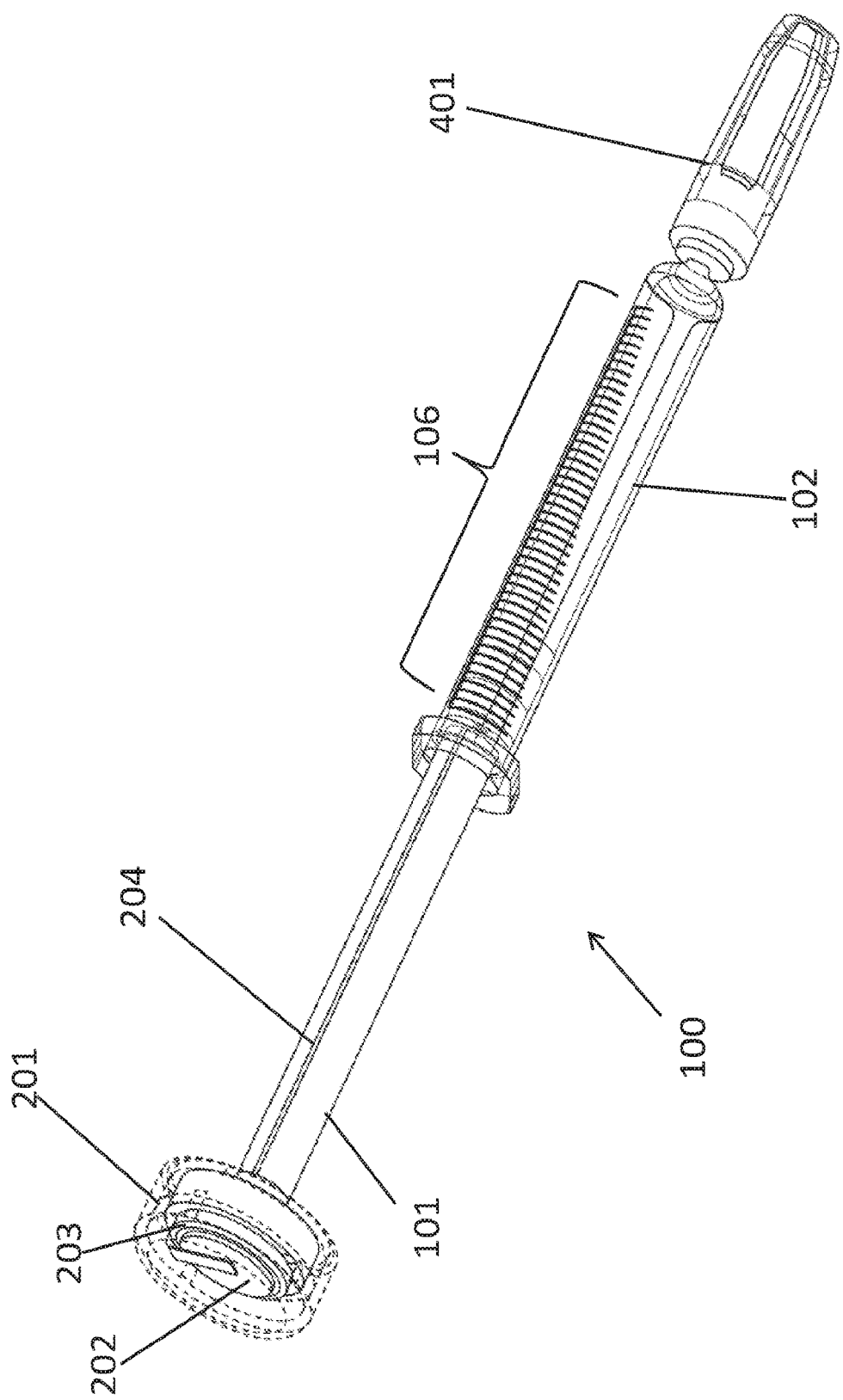
FIG. 4 is a perspective view of the plunger of FIG. 2 and the syringe barrel of FIG. 3 assembled together as part of a syringe system, in accordance with a preferred embodiment of the present invention.

FIG. 4 illustrates an assembled syringe system 100, in accordance with aspects described herein. The plunger 101 is shown inserted into the syringe barrel 102 such that the coil 108 interacts with the label 106. Eddy currents generated in the coil 108 are communicated over the electrical leads 204 to be processed by the microcontroller 105 (not shown in FIG. 4) housed on the circuit board 203 and located in the head portion 201 of the plunger 101. In certain aspects, a safety cover 401 may be used to cover the needle 301 or drug delivery mechanism during transport and before use.

The syringe system 100 preferably allows healthcare providers to automatically monitor the state of the low-cost injection device, which enables them to track dosing regimen adherence, shelf-life evaluation, plunger movement during transportation, and cold chain integrity.

The technology may also be implemented into more complex injection devices that already include wireless connectivity. Autoinjectors which utilizes a moving plunger 101 and a syringe barrel 102 may incorporate features of the disclosure described herein. The syringe barrel 102 may be made of materials that do not interfere with the magnetic field created by the coil, such as polymers, ceramics, and some metals. On-body or wearable injectors could also accommodate the technology described herein. In addition, this technology may be particularly relevant for syringes that utilize a safety system.

Further, the syringe system 100 may also be used in a hospital environment to communicate automatically with the hospital inventory management system, such that the syringe use may be tracked in real-time and re-ordered automatically based on a pre-set inventory level.

The syringe system 100 may be produced by overmolding or insert-molding the microcontroller 105, battery 102, and electrical conductors into the plunger 101, as described throughout this disclosure. This may be done during a general injection molding process.

The label 106 may be applied to the syringe barrel 102 using any conventional syringe labeling equipment. The piston 206 may also contain elements of the electrical system, such as the coil 108, so that when the plunger 101 is assembled to the piston 108, it may complete the electrical circuit. In some aspects, some of the electrical components may be contained within a syringe flange adaptor (not shown), or in the surrounding components of an autoinjector or wearable on-body drug delivery system.

Embodiments of the present invention may also be used in a similar fashion with existing self-injection devices, like a prefilled syringe. The movement of the plunger 101 and/or temperature of the device may be detected by the microcontroller 105. The microcontroller 105 may read and record the information, then may transmit the information to a smart device 103 via, for example, BLE communication. The external device 103 may have a connected application to read, record, and display the information from the syringe system 100. This information may also be relayed to healthcare providers and other stakeholders.

These aspects are not meant to be limiting. For different injector systems, the positioning and size of the circuit may vary. It will be appreciated by persons skilled in the art that the present disclosure is not limited by what has been particularly shown and described hereinabove. Rather the scope of the present disclosure includes both combinations and sub-combinations of various features described hereinabove as well as modifications and variations which would occur to persons skilled in the art upon reading the foregoing description and which are not in the prior art.

What is claimed is:

1. A syringe system, comprising:
    a plunger including:
        a microcontroller,
        a battery, and
        a coil connected to the microcontroller and the battery by two or more electrical leads; and
    a syringe barrel having a proximal end, a distal end, and a cylindrical sidewall defining a longitudinal axis, the cylindrical sidewall extending longitudinally between the proximal and distal ends, the sidewall having an exterior surface and defining an internal volume, the plunger being positioned between the proximal and distal ends of the syringe barrel and being movable within the internal volume with respect to the syringe barrel in the longitudinal direction, the syringe barrel further including:
        a label disposed on the sidewall having at least two conductive strips extending in a non-parallel direction with respect to the longitudinal axis having unique lengths;
    wherein the microcontroller is configured to determine a position of the plunger with respect to the syringe barrel by measuring a current induced in the coil by the at least two conductive strips.

2. The system of claim 1, wherein the plunger includes a head section, at least a portion of which extends outside of the syringe barrel, and the battery and the microcontroller are disposed in the head section.

3. The system of claim 1, further including a temperature sensor configured to output a signal representative of a temperature of the syringe system to the microcontroller.

4. The system of claim 3, further including a wireless communication interface, the microcontroller being configured to transmit the temperature data received from the temperature sensor to a smart device via the wireless communication interface.

5. The system as recited in claim 1, further including a wireless communication interface, the microcontroller being configured to transmit plunger position data to an external device via the wireless communication interface.

6. The system as recited in claim 5, wherein the external device is configured to provide an alert to a user if the plunger position is determined by the microcontroller to have moved in excess of a predetermined distance.

7. The system as recited in claim 1, wherein the microcontroller is configured to periodically cause the battery to supply current to the coil at predetermined intervals.

8. The system as recited in claim 1, wherein the at least two conductive strips are transparent.

9. The system as recited in claim 1, wherein the at least two of the conductive strips are arranged on the sidewall of the barrel so as to be spaced apart from one another in the longitudinal direction, and are arranged in order according to circumferential length.

10. A method of using a syringe system including a plunger having a microcontroller, a battery, and a coil connected to the microcontroller and battery by two or more electrical leads, a syringe barrel defining a longitudinal axis and receiving the plunger, and a label disposed on a sidewall of the syringe barrel and having at least two conductive strips extending in a non-parallel direction with respect to the longitudinal axis and having unique lengths, the method comprising:
    generating, by the microcontroller, an eddy current in the coil by causing the battery to supply a current to the coil via the two or more electrical leads, whereby an amplitude of the generated eddy current depends on a relative position of the coil with respect to the at least two conductive strips of the label along a longitudinal direction of the syringe barrel;
    measuring, by the microcontroller, the generated eddy current in the coil via the two or more electrical leads; and
    determining, by the microcontroller based on the measured eddy current, a position of the plunger with respect to the syringe barrel.

11. The method of claim 10, further comprising:
    transmitting, by the microcontroller via a wireless communication interface, data regarding the determined plunger position to an external device.

12. The method of claim 11, further comprising:
    generating, by the external device, one or more alerts based on data regarding the plunger position.

13. The method of claim 10, further comprising:
    generating, by a temperature sensor, temperature data based on a measured temperature of the syringe system; and
    transmitting, by the microcontroller via a wireless communication interface, the temperature data to an external device.

14. The method of claim 13, further comprising:
    generating, by the external device, one or more alerts based on the temperature data.

* * * * *